United States Patent [19]
van der Merwe

[11] Patent Number: 6,113,617
[45] Date of Patent: Sep. 5, 2000

[54] DISPOSABLE SCALPEL

[75] Inventor: Marius van der Merwe, Western Cape, South Africa

[73] Assignee: Harwill Industries (PTY) Ltd., Western Cape, South Africa

[21] Appl. No.: 09/068,834

[22] PCT Filed: Nov. 20, 1996

[86] PCT No.: PCT/GB96/02863

§ 371 Date: Oct. 20, 1998

§ 102(e) Date: Oct. 20, 1998

[87] PCT Pub. No.: WO97/18764

PCT Pub. Date: May 29, 1997

[30] Foreign Application Priority Data

Nov. 21, 1995 [ZA] South Africa .......................... 95/9848

[51] Int. Cl.[7] .................................................. A61B 17/32
[52] U.S. Cl. .......................... 606/167; 606/185; 30/156; 30/155
[58] Field of Search .................................... 606/167, 185; 30/129–131, 151, 156, 161, 160, 47, 53, 286, 155; 76/82

[56] References Cited

U.S. PATENT DOCUMENTS

| | | | |
|---|---|---|---|
| 2,820,291 | 1/1958 | Philippar ..................................... | 30/161 |
| 3,306,297 | 2/1967 | Voorhees et al. ........................ | 606/167 |
| 4,083,110 | 4/1978 | Goldin et al. .............................. | 30/155 |
| 4,719,915 | 1/1988 | Porat et al. ............................. | 128/305 |
| 4,825,545 | 5/1989 | Chase et al. .............................. | 30/153 |

*Primary Examiner*—Corrine McDermott
*Assistant Examiner*—Jennifer Maynard
*Attorney, Agent, or Firm*—Birch, Stewart, Kolasch & Birch, LLP

[57] ABSTRACT

This invention relates to a medical scalpel (10) that comprises a grip (20) and a scalpel blade (30) located on a blade carrier (40). The grip (20) and the blade carrier (40) are hingedly connected to each other by means of a hinge formation extending transversely to the principal axis of the scalpel. The blade carrier (40) is rotatable between an operative position, in which the blade (30) is exposed for use, and an inoperative position, in which the blade (30) is retained in a recess (22) formed in the grip (20). The blade carrier (40) is preferably adapted for one time rotation to and retention in the inoperative position of the blade (30) by engagement formations formed in corresponding surfaces of the blade carrier (40) and the grip (20). The scalpel is integrally moulded in injection moulded plastics material in which the hinge formation is constituted by an integrally moulded line of weakness (50) formed between the blade carrier and the grip.

10 Claims, 3 Drawing Sheets

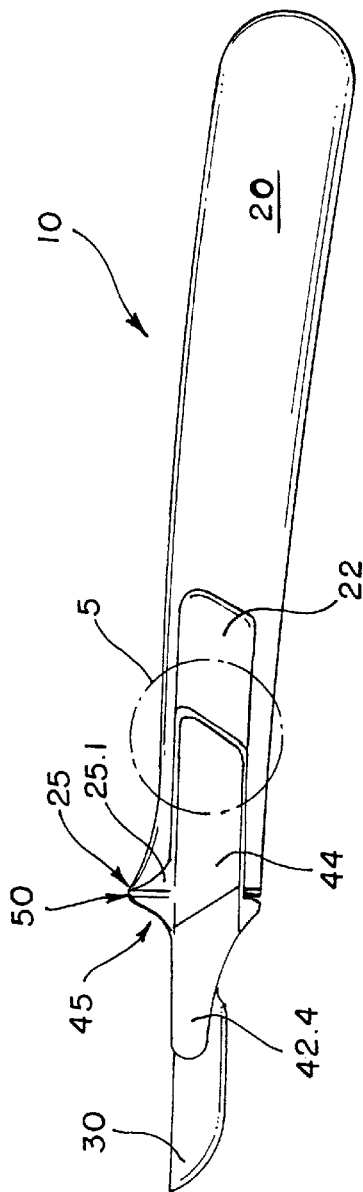
FIG. 4
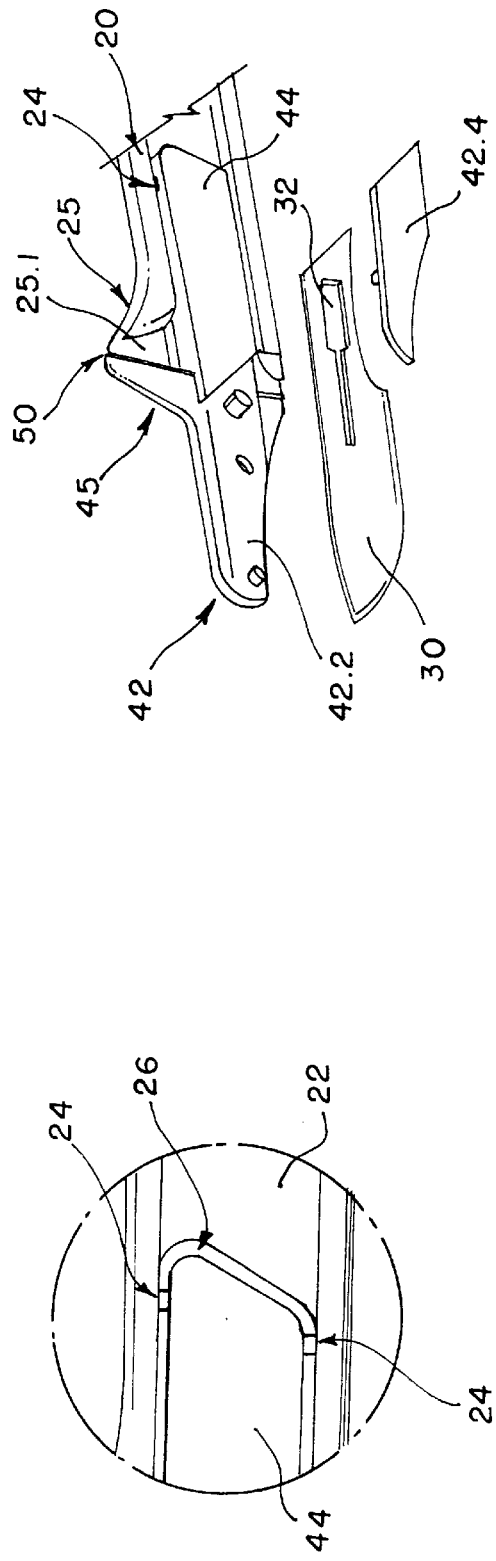
FIG. 6
FIG. 5

DISPOSABLE SCALPEL

This application is the national phase under 35 U.S.C. §371 of prior PCT International Application No. PCT/GB96/02863, which has an International filing date of Nov. 20, 1996, which designated the United States of America.

BACKGROUND TO THE INVENTION

The present invention relates to a medical scalpel.

Cutting instruments, such as medical scalpels used in current surgical procedures normally comprise a metallic handle with a specifically designed front end to which a blade is attached. The blade is normally attached by sliding its female slot onto a male track located on the front end of the handle. The attachment and the removal of the blade is difficult and often results in injury or in the blade slipping off.

Recent advances in this field include the manufacture of disposable handles which allow the user to dispose of the blade and handle without disengaging the blade from the handle. This decreases the chances of injury to the user but the blade remains unprotected and poses a threat to those handling the scalpel after use.

While U.S. Pat. No. 3,306,297—Voorhees is directed to a tracheotomy set, it does describe a scalpel blade mounted on a blade carrier that pivots to fold the blade away. The tracheotomy set can therefore be folded away so that it can be carried around in a pocket for use in emergencies. The blade pivots on a pivot axis that extends transversely to the principal axis of the scalpel blade plane to provide a folding action comparable to that of a penknife with the result that the scalpel blade pivots in the blade plane with a cutting motion. This makes the Voorhees device unsuitable for use as a surgical instrument for regular use.

Other developments in this field include blade removing devices which allow a more convenient and safe way of removing the blade from the handle before disposing the blade. These devices are separate from the handle and the user does not always have it on hand when needed. These devices also inflate the costs of the scalpels.

Another development in this field includes the use of safety blade sheaths which are fitted to the scalpel handle. The sheaths are flipped or slid in the forward direction to cover the blade after use. Again, these devices are not moulded as an integral part of the scalpel and therefore inflate the costs of the scalpel. They also interfere with the grip of the scalpel.

It is the object of the present invention to address these problems.

SUMMARY OF THE INVENTION

According to the present invention, a scalpel comprises a grip and a blade carrier for a substantially planar scalpel blade, the blade carrier being hingedly connected to the grip by means of a hinge formation that extends transversely to the principal axis of the scalpel, the hinge formation being adapted to permit hinged rotation of the blade carrier between an operative position in which a scalpel blade that may be secured to the blade carrier is exposed for use and an inoperative position in which the scalpel blade is retained in a recess formed in the grip, characterised in that the hinge axis of the hinge formation is co-extensive with the plane of the scalpel blade.

The scalpel may be integrally moulded in injection moulded plastics in which event the hinge formation may be constituted by an integrally moulded line of weakness formed between the blade carrier and the grip.

In one form of the invention, the scalpel includes means to retain the blade carrier in the operative position of the present scalpel blade, the retaining means being constituted by one or more frangible webs integrally moulded to extend between parts of the blade carrier and the grip that are adjacent to one another in the operative position and that tend to move apart when, in use, the blade carrier is hinged to the inoperative position thereof.

The engagement formations on the grip may be constituted by the broken web portions.

In this form of the present invention, the blade carrier includes proximal and distal ends on either side of the hinge formation, the distal end of the blade carrier being adapted to receive the blade and the proximal end thereof being constituted by a blade carrier body that is separate from and co-extensive with the grip in the operative position of the blade and retained in the grip by the frangible web, hinged rotation of the blade carrier body when, in use, the blade carrier is hinged to the inoperative position, resulting in the frangible webs being broken to permit rotation of the distal end of the blade carrier into the void formed in the grip by the displaced blade carrier body, the engagement formation on the grip being engageable with the engagement formation on the distal end of the blade carrier to retain the blade in the recess in the grip.

The engagement formations may be constituted by one or more recesses formed in the distal end of the blade carrier and corresponding projections extending from the grip, the projections being adapted complementally to engage the recesses. Alternatively, the engagement formations may be constituted by one or more recesses formed in the grip and corresponding projections extending from the distal end of the blade carrier, the projections being adapted complementally to engage the recesses.

The scalpel may conveniently be adapted to accept a conventional scalpel blade that is removably securable to the blade carrier by means of an interengageable slot and key formations formed, respectively, on the blade and blade carrier. To this end, the blade carrier may include a blade seat and an engagement member that is engageable with the seat through appropriately positioned apertures in the blade to secure a conventional blade to the blade carrier.

As an alternative the to this embodiment of the present invention, the scalpel may be adapted to accept a conventional scalpel blade that is permanently secured to the blade carrier, the blade being adhered to the blade carrier by means of adhesives, welding or by moulding into the injection moulded plastics blade carrier.

In the preferred form of the invention, the scalpel is disposable, in which event the blade carrier may be adapted for one time rotation to and relatively secure retention in the inoperative position of the blade, the engagement formations formed in the blade carrier and the grip being adapted to lock the blade carrier in the inoperative position of the blade.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 4 is a side elevation of the scalpel of FIG. 1 in the operative position.

FIG. 5 is a detailed side elevation of an encircled area 5 in FIG. 4;

FIG. 6 is an exploded diagrammatic perspective view of a blade carrier of the scalpel of FIG. 1 depicting the manner in which the blade is secured thereto.

DETAILED DESCRIPTION OF PREFERRED EMBODIMENTS OF THE INVENTION

Figure 1:
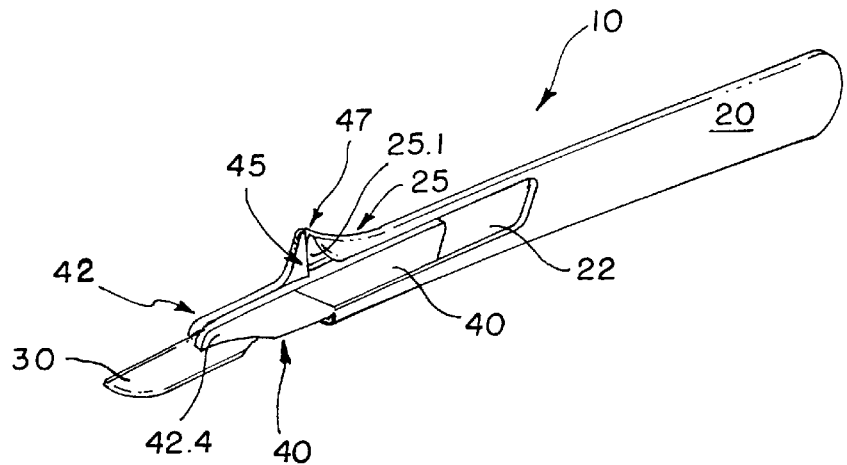
FIG. 1 is a diagrammatic perspective view of a scalpel according to the invention, in an operative position.

The present invention will be described with reference to the disposable medical scalpel 10 illustrated in the drawings.

FIG. 1 illustrates a medical scalpel 10 that includes a grip 20 and a scalpel blade 30 located on a blade carrier 40.

The grip 20 and the blade carrier 40 are provided with complementary parts 25, 45 of a hilt crosspiece formation 47 intended partly to improve the grip of the scalpel 10. In addition, the grip 20 and the blade carrier 40 are hingedly connected to each other by means of a hinge formation extending transversely to the principal axis of the scalpel through the crosspiece 47, the enlarged area of which serves to increase the hinge area.

The scalpel is integrally moulded in injection moulded plastics material in which the hinge formation is constituted by an integrally moulded line of weakness 50 formed between the blade carrier and the grip.

Figure 3:
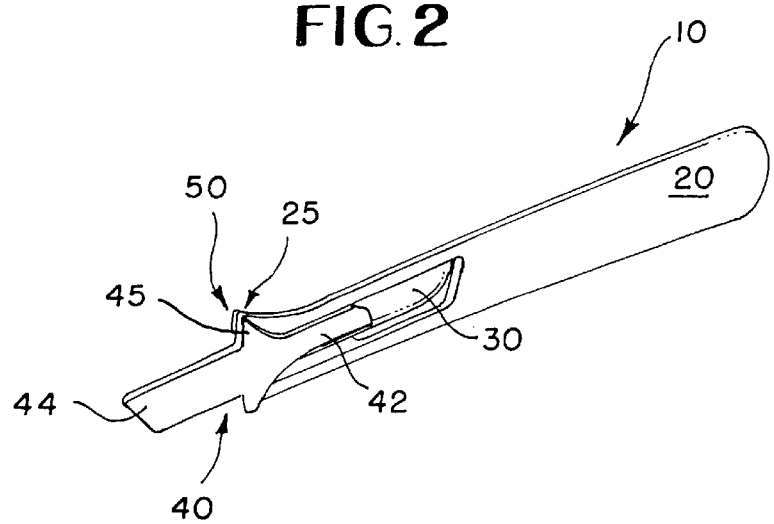
FIG. 3 is a diagrammatic isometric view of the scalpel of FIG. 1 in the inoperative position.

The blade carrier 40 is rotatable between an operative position, in which the blade 30 is exposed for use, as is illustrated in FIG. 1, and an inoperative position, in which the blade 30 is retained in a recess 22 formed in the grip 20, as is illustrated in FIG. 3.

The blade carrier 40 is preferably adapted for one time rotation to retention in the inoperative position of the blade 30 by engagement formations formed in corresponding surfaces of the blade carrier and the grip 20, as will be explained later in this specification.

In another form of the present invention, the blade carrier is adapted for repeated rotation to and from the inoperative position of the blade. In this form of the present invention, the inoperative position of the blade, by means of engagement formations formed in corresponding surfaces of the blade carrier and the grip.

The blade carrier 40 includes proximal and distal ends on either side of the hinge formation 50. The distal end 42 of the blade carrier 40 is adapted to receive the blade 30 and the proximal end is constituted by a blade carrier body 44 separate from and co-extensive with the grip 20 when the blade carrier 40 is in the operative position of the blade 30.

The blade carrier body 44 is retained in the grip 20 by retaining means constituted by frangible webs 24 integrally moulded to extend between the blade carrier body 44 and the grip 20, as is illustrated in FIG. 5.

In addition, or alternatively, the frangible webs may be integrally moulded to extend across the hinge formation 50.

Hinged rotation of the blade carrier body 44 when, in use, the blade carrier 40 is hinged to the inoperative position, results in the frangible webs 24 being broken to permit rotation of the distal end 42 of the blade carrier 40 into a void 26 formed in the grip 20 by the displaced blade carrier body 44.

The blade 30 is a conventional scalpel blade removably securable to the blade carrier 40 by means of the interengageable slot and key formations formed, respectively, on the blade 30 and blade carrier 40. The blade carrier 40 includes a blade seat 42.2 and an engagement member constituted by a cover plate 42.4 that is engageable with the seat 42.2 through an appropriately positioned aperture 32 in the blade 30 to secure the blade 30 to the blade carrier 40 in spigot and socket fashion, as is illustrated in FIG. 6.

Figure 7:
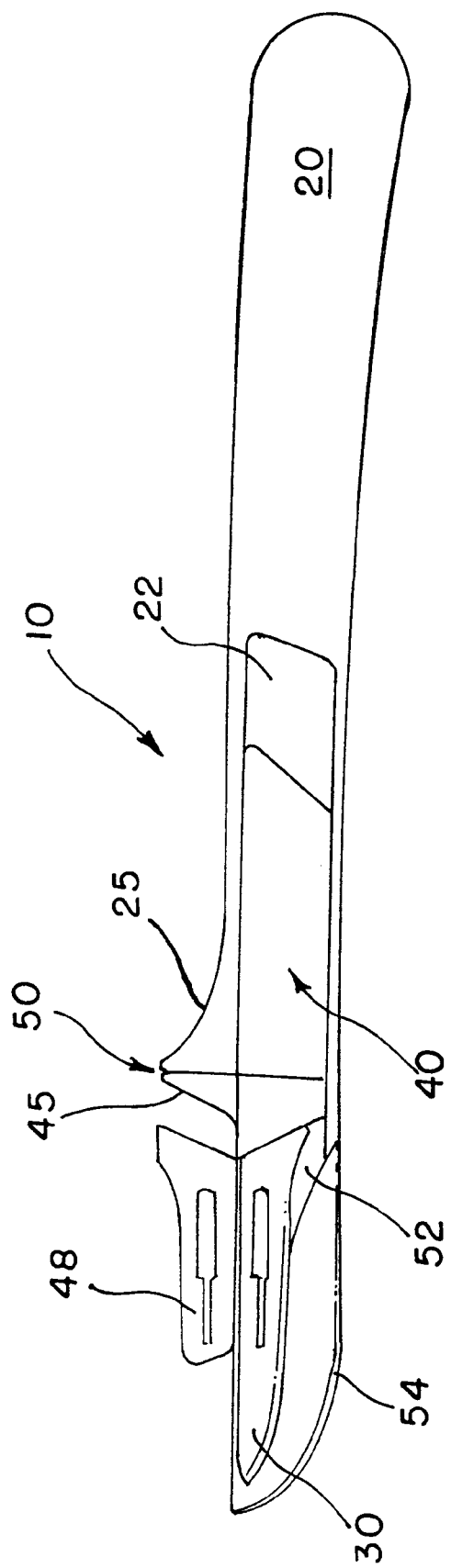
FIG. 7 is a diagrammatic perspective view of another embodiment of a scalpel according to the invention, in an operative position.

FIG. 7 illustrates an alternative scalpel in which the blade 30 is secured to the blade carrier 40 by means of an interengageable slot and key formations formed, respectively, on the blade 30 and blade carrier 40. The blade carrier 40 is provided with a cover flap 48 having corresponding engagement formations, the cover flap 48 being hingedly attached to the blade carrier 40 to encase the blade 30 when it is secured to a corresponding surface 52 on the blade-carrier 40.

The blade carrier 40 is also provided with a protective blade sheath 54.

Alternatively, the blade may be welded or adhered to the blade carrier. In a further alternative, the blade may be moulded into the injection moulded plastics blade carrier.

In use, the disposable medical scalpel 10 is packaged with the blade 30 (in the operative position) in a sterile package. Where the blade carrier 40 is adapted for one time rotation from the operative position to the inoperative position, the blade 30 is exposed for use with the blade carrier 40 locked in position by the frangible webs 24.

Where the blade carrier 40 is adapted for repeated rotation, the scalpel can be packaged with the blade 30 in the inoperative position. Before use, the blade carrier 40 will be rotated to and locked in the operative position.

Figure 2:
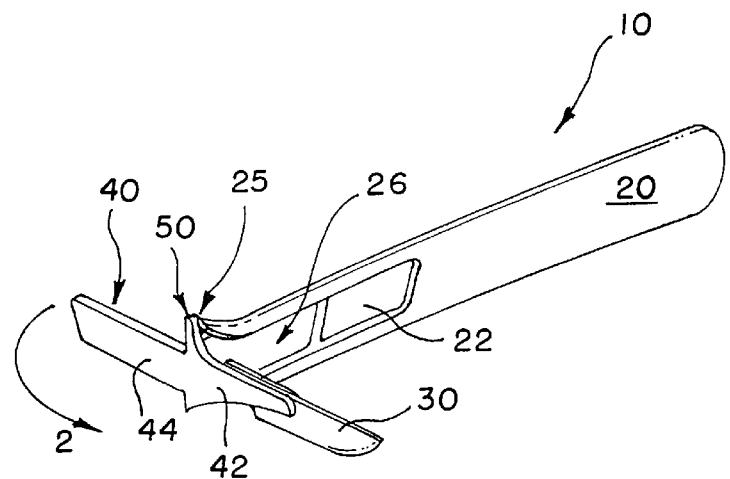
FIG. 2 is a diagrammatic perspective view of the scalpel of FIG. 1 in a position intermediate the operative and an inoperative position.

Upon completion of the intended surgical procedure, pressure is applied to the blade carrier 40. In order to apply sufficient pressure to break the frangible webs 24 between the blade carrier body 44 and the grip, the user need merely press the blade 30 and blade carrier 40 hard against a table or other surface. Breaking of the webs 24 permits rotation of the blade carrier 40 through 180 degrees in the direction of arrow 2 in FIG. 2. This the user does by "folding" the scalpel 10 while holding onto the grip 20. This results in rotation of the distal end 42 of the blade carrier 40 into the void 26 formed in the grip 20 by the displaced blade carrier body 44. Sufficient pressure is then applied to the blade carrier body 44 by banging the scalpel 10, for instance, to lock the blade carrier 40 in the inoperative position of the blade. This is done by the engagement of locking formations formed on corresponding parts of the blade carrier 40 and the grip 20 as the blade carrier 40 is pressed home into the void 26 in the grip 20.

The locking formations (not shown) may be constituted by clip formations or the like constituted by an enlargement on the blade carrier 40 that engages forcibly with a complemental recess formed in the grip 20 in the area surrounding the void 26.

Alternatively, the locking formations may be constituted by an enlargement on the grip 20 that locks into a depression formed in the blade carrier 40 or the locking formations may be constituted by mating friction surfaces.

In each case, the locking formations are dimensioned to engage with each other securely to prevent the scalpel 10 from being reused.

The crosspiece portion 25 on the grip side of the hinge formation 50 is formed with a recess 25.1 that is complementary with the crosspiece portion 45. The recess 25.1 houses the crosspiece portion 45 in the inoperative position of the blade carrier 40, thereby permitting full rotation of the blade carrier to the inoperative position thereof.

The crosspiece portion 25 serves as an abutment against which the crosspiece portion 45 abuts to prevent the blade carrier 40 from rotating more than 180 degrees. In addition, the blade 30 butts up against the recess 22 in the grip.

In the process of securing the scalpel 10 for disposal, the practitioner need not release the grip 20 until the blade 30 is out of harm's way.

What is claimed is:

1. A scalpel comprising a grip and a blade carrier for a substantially planar scalpel blade, the blade carrier being hingedly connected to the grip by means of a hinge formation that extends transversely to a principal axis of the scalpel, the blade carrier including proximal and distal ends on either side of the hinge formation with the distal end of the blade carrier being adapted to receive the blade and the proximal end thereof being constituted by a blade carrier body that is separate from and co-extensive with the grip in an operative position of the blade, the hinge formation being adapted to permit hinged rotation of the blade carrier between the operative position of the blade and an inoperative position thereof in which the distal end of the blade carrier is retained in a void formed in the grip by hingedly displacing the blade carrier from the operative position, and wherein the hinge axis of the hinge formation is adapted to be co-extensive with a plane of the scalpel blade.

2. A scalpel according to claim 1 which is integrally moulded in injection moulded plastics, the hinge formation being constituted by an integrally moulded line of weakness formed between the blade carrier and the grip.

3. A scalpel according to claim 2 including means to retain the blade carrier in the operative position of the scalpel blade, the retaining means being constituted by one or more frangible webs integrally moulded to extend between parts of the blade carrier and the grip that are adjacent to one another in the operative position and that tend to move apart when, in use, the blade carrier is hinged to the inoperative position thereof.

4. A scalpel according to claim 3 in which the engagement formations are constituted by one or more recesses formed in the distal end of the blade carrier and corresponding projections extending from the grip, the projections being adapted complementally to engage the recesses.

5. A scalpel according to claim 4 in which the engagement formations are constituted by one or more recesses formed in the grip and corresponding projections extending from the distal end of the blade carrier, the projections being adapted complementally to engage the recesses.

6. A scalpel according to claim 1 that is adapted to accept a ambiguous scalpel blade that is removably securable to the blade carrier by means of interengageable slot and key formations formed, respectively, on the blade and blade carrier.

7. A scalpel according to claim 6 in which the blade carrier includes a blade seat and an engagement member that is engageable with the seat through appropriately positioned aperture in the blade to secure a blade to the blade carrier.

8. A scalpel according to claim 1 that is adapted to accept a conventional scalpel blade that is permanently secured to the blade carrier, the blade being adhered to the blade carrier by means of adhesives, welding or by moulding into the blade carrier.

9. A scalpel according to claim 4 that is disposable, the blade carrier being adapted for one time rotation to and relatively secure retention in the inoperative position of the blade, the engagement formations formed in the blade carrier, and the grip being adapted to lock the blade carrier in the inoperative position of the blade.

10. A scalpel according to claim 3 in which hinged rotation of the blade carrier body results in the frangible webs being broken to permit rotation of the distal end of the blade carrier into void formed in the grip by the displaced blade carrier body, an engagement formation on the grip being engageable with an engagement formation on the distal end of the blade carrier to retain the blade in the recess in the grip.

* * * * *